(12) United States Patent
Song

(10) Patent No.: US 10,150,252 B2
(45) Date of Patent: Dec. 11, 2018

(54) METHOD OF RECOUPLING COMPONENTS DURING REPROCESSING

(71) Applicant: Stryker Sustainability Solutions, Inc., Tempe, AZ (US)

(72) Inventor: Chuanzhe Song, Avondale, AZ (US)

(73) Assignee: Stryker Sustainability Solutions, Inc., Tempe, AZ (US)

(*) Notice: Subject to any disclaimer, the term of this patent is extended or adjusted under 35 U.S.C. 154(b) by 498 days.

(21) Appl. No.: 14/861,129

(22) Filed: Sep. 22, 2015

(65) Prior Publication Data

US 2016/0082649 A1   Mar. 24, 2016

Related U.S. Application Data

(60) Provisional application No. 62/054,046, filed on Sep. 23, 2014.

(51) Int. Cl.
*B29C 73/00* (2006.01)
*B32B 43/00* (2006.01)
(Continued)

(52) U.S. Cl.
CPC .......... *B29C 66/876* (2013.01); *B29C 65/524* (2013.01); *B29C 65/7841* (2013.01); *B29C 66/1122* (2013.01); *B29C 66/21* (2013.01); *B29C 66/232* (2013.01); *B29C 66/69* (2013.01); *B29C 66/72321* (2013.01); *B29C 66/836* (2013.01); *B29C 66/8432* (2013.01); *A61B 2562/225* (2013.01); *B29C 65/483* (2013.01); *B29C 65/527* (2013.01); *B29C 66/71* (2013.01);
(Continued)

(58) Field of Classification Search
CPC ....... B29C 65/48; B29C 65/52; B29C 65/524; B29C 65/54; B29C 65/542; B29C 66/02; B29C 66/022; B29C 66/0224; B29C 66/02245; B29C 66/028; B29C 66/21; B29C 66/301; B29C 66/69; H01B 7/0853
USPC ..... 156/60, 94, 98, 152, 153, 166, 180, 181, 156/247, 272.2, 273.9, 290, 291, 296, 156/305; 174/113 R, 117 R, 117 F, 174/117 A; 264/36.19
See application file for complete search history.

(56) References Cited

U.S. PATENT DOCUMENTS 1,729,160 A   9/1929 Engle
2,628,998 A   2/1953 Frisbie
(Continued)

FOREIGN PATENT DOCUMENTS

EP   0097414 A  *  1/1984   ............... H01B 7/08
EP   1 273 922 A1   1/2003
EP   1792637 A2  *  6/2007   ......... B29C 47/0023

*Primary Examiner* — Philip C Tucker
*Assistant Examiner* — Brain R Slawski
(74) *Attorney, Agent, or Firm* — Howard & Howard Attorneys PLLC

(57) ABSTRACT

A method of recoupling components of a medical device in a desired orientation during reprocessing of the medical device. The method uses a binder to return the components to an adhered condition from a separated condition. The method comprises receiving the components of the medical device in the separated condition with the component spaced from the desired orientation. The components of the medical device are cleaned and arranged in the desired orientation. The binder is applied to recouple the components in the desired orientation to return the components to the adhered condition.

22 Claims, 13 Drawing Sheets

(51) Int. Cl.
    *B29C 65/00*     (2006.01)
    *B32B 37/00*     (2006.01)
    *B32B 38/10*     (2006.01)
    *B32B 7/14*     (2006.01)
    *C09J 5/00*     (2006.01)
    *H01B 7/08*     (2006.01)
    *B29C 65/52*     (2006.01)
    *B29C 65/78*     (2006.01)
    *B29L 31/34*     (2006.01)
    *B29L 31/00*     (2006.01)
    *B29C 65/48*     (2006.01)
    *B29K 105/26*     (2006.01)

(52) U.S. Cl.
    CPC ... *B29K 2105/26* (2013.01); *B29L 2031/3462* (2013.01); *B29L 2031/753* (2013.01)

(56) References Cited

U.S. PATENT DOCUMENTS

| | | | |
|---|---|---|---|
| 2,666,093 A | | 1/1954 | Wildberg |
| 2,716,623 A | | 8/1955 | Tator |
| 2,729,696 A | | 1/1956 | Mapelsden et al. |
| 2,749,261 A | | 6/1956 | Hardison |
| 3,134,845 A | | 5/1964 | George |
| 3,513,609 A | | 5/1970 | Lang |
| 4,091,062 A | | 5/1978 | Nelson |
| 4,113,335 A | | 9/1978 | Lang et al. |
| 4,145,176 A | | 3/1979 | Nelson |
| 4,154,977 A | | 5/1979 | Verma |
| 4,162,183 A | * | 7/1979 | Estes ............ B29C 65/00 156/157 |
| 4,218,417 A | | 8/1980 | Jacquemart |
| 4,486,253 A | * | 12/1984 | Gonia ............ B29C 66/69 156/305 |
| 4,627,942 A | | 12/1986 | Gagen et al. |
| 4,729,628 A | | 3/1988 | Kraft et al. |
| 4,783,579 A | | 11/1988 | Brandolf et al. |
| 5,010,642 A | * | 4/1991 | Takahashi ........ H01B 13/01254 140/147 |
| 5,093,048 A | | 3/1992 | Kagan |
| 5,147,510 A | | 9/1992 | Iura et al. |
| 5,286,924 A | | 2/1994 | Loder et al. |
| 5,296,648 A | | 3/1994 | Johnson |
| 5,371,823 A | | 12/1994 | Barrett et al. |
| 5,442,722 A | | 8/1995 | DeCarlo |
| 5,606,151 A | | 2/1997 | Siekierka |
| 5,724,984 A | | 3/1998 | Arnold et al. |
| 5,949,947 A | | 9/1999 | Eslambolchi et al. |
| 5,973,268 A | | 10/1999 | Cheng |
| 6,057,511 A | | 5/2000 | Ikeda et al. |
| 6,111,202 A | | 8/2000 | Martin |
| 6,112,400 A | | 9/2000 | Frater et al. |
| 6,249,628 B1 | | 6/2001 | Rutterman et al. |
| 6,273,977 B1 | | 8/2001 | Harden et al. |
| 6,370,303 B1 | | 4/2002 | Fitz et al. |
| 6,485,593 B1 | * | 11/2002 | Christoffersen ...... A61M 39/18 156/157 |
| 6,734,364 B2 | | 5/2004 | Price et al. |
| 6,841,729 B2 | | 1/2005 | Sakabe et al. |
| 6,861,590 B2 | | 3/2005 | Rossi |
| 6,928,217 B2 | | 8/2005 | Mohler et al. |
| 7,049,523 B2 | | 5/2006 | Shuman et al. |
| 7,206,481 B2 | | 4/2007 | Quinn et al. |
| 7,259,332 B2 | | 8/2007 | Shuman et al. |
| 7,358,436 B2 | | 4/2008 | Dellagala et al. |
| 7,696,437 B2 | | 4/2010 | Clark et al. |
| 7,777,135 B2 | | 8/2010 | Howe |
| 8,180,425 B2 | | 5/2012 | Silvitelli et al. |
| 8,404,976 B2 | | 3/2013 | Telley et al. |
| 8,399,769 B2 | | 5/2013 | Doll |
| 8,548,294 B2 | | 10/2013 | Toge et al. |
| 8,560,043 B2 | | 10/2013 | Selvitelli et al. |
| 8,571,627 B2 | | 10/2013 | Tremblay et al. |
| 8,595,922 B2 | | 12/2013 | Lind et al. |
| 2005/0173148 A1 | | 8/2005 | Shuman et al. |
| 2011/0293229 A1 | | 12/2011 | Hurley et al. |
| 2013/0079611 A1 | * | 3/2013 | Besko ............ A61B 5/14552 600/344 |
| 2013/0085368 A1 | | 4/2013 | Coggins |
| 2013/0153112 A1 | | 6/2013 | Telley et al. |

* cited by examiner

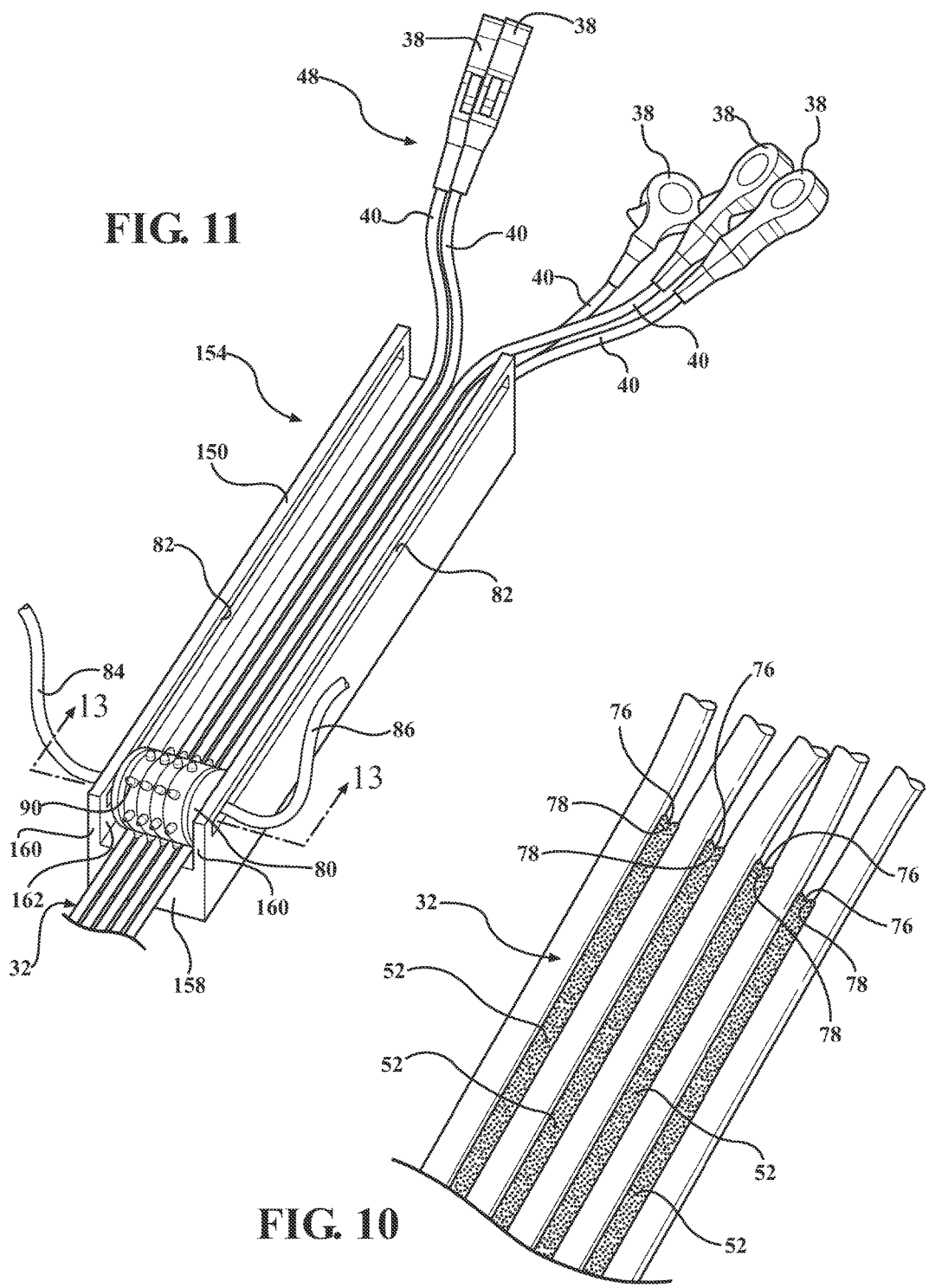

METHOD OF RECOUPLING COMPONENTS DURING REPROCESSING

CROSS REFERENCE TO RELATED APPLICATIONS

This application claims the benefit of U.S. Provisional Application No. 62/054,046, filed on Sep. 23, 2014, the disclosure of which is incorporated by reference herein.

TECHNICAL FIELD

The present invention generally relates to a method of recoupling components of a medical device in a desired orientation during reprocessing of the medical device.

BACKGROUND

There is a desire during reprocessing of medical devices to recouple components of a medical device in a desired orientation so that the medical device is restored to a reusable condition. One example of a medical device that is often reprocessed is a cable assembly that includes a plurality of strands that are coupled together. The plurality of strands are separated from each other during use. A current method of recoupling the plurality of strands in the desired orientation during reprocessing requires an operator to use a clip or wire tie to loosely connect the plurality of strands. An end user must remove the clip or wire tie to separate the plurality of strands from each other. One problem is that the clip or wire tie may fall off during handling resulting in the plurality of strands becoming tangled with each other and requiring the end user to untangle the plurality of strands. Another problem is that the end user has an additional step of removing the clip or wire tie to separate the plurality of strands from each other before the medical device can be used.

Another example of a medical device that is often reprocessed is an intravenous device including a bag and a tube separated from the bag. A current method of recoupling the tube and bag in the desired orientation requires an operator to use a piece of tape to loosely connect the tube and bag. An end user must remove the tape in order to separate the tube from the bag. One problem is that the tape may fall off during handling or may be inadvertently removed allowing the tube and bag to become separated from each other. Another problem is that the end user has an additional step of removing the tape to separate the tube from the bag.

Thus, there remains an opportunity to develop a method of recoupling components of a medical device in a desired orientation during reprocessing of the medical device that reduces some of the problems of the methods noted herein.

SUMMARY OF THE DISCLOSURE

One non-limiting example of a method for recoupling components of a medical device in a desired orientation during reprocessing of the medical device uses a binder to return the components to an adhered condition from a separated condition. The method comprises receiving the components of the medical device in the separated condition with the components spaced from the desired orientation. The components of the medical device are cleaned and arranged in the desired orientation. The binder is applied to recouple the components in the desired orientation to return the components to the adhered condition.

Another non-limiting example of a method for recoupling a plurality of strands of a used cable assembly in a desired orientation uses a fixture and a binder. The used cable assembly includes a fitting attached to a first end of each of the plurality of strands. The plurality of strands of the used cable assembly are cleaned and arranged in the desired orientation using the fixture. The binder is applied on the plurality of strands to recouple the plurality of strands in the desired orientation. The plurality of strands are removed from the fixture.

Advantageously, because the binder recouples the plurality of strands to each other, the plurality of strands will not become tangled with each other. Additionally, because the binder recouples the plurality of strands to each other, there is no additional step of removing the clip or wire tie before use of the medical device.

BRIEF DESCRIPTION OF THE DRAWINGS

Referring now to the drawings, exemplary illustrations are shown in detail. Although the drawings represent representative examples, the drawings are not necessarily to scale and certain features may be exaggerated to better illustrate and explain an innovative aspect of an illustrative example. Further, the exemplary illustrations described herein are not intended to be exhaustive or otherwise limiting or restricting to the precise form and configuration shown in the drawings and disclosed in the following detailed description. Exemplary illustrations are described in detail by referring to the drawings as follows:

FIG. 10 is an enlarged partial perspective view of the binder of FIG. 9, illustrating a tear cavity defined in the plurality of ends of the binder;

FIG. 11 is a top perspective view of another non-limiting example of the coupling device including a fixture and a container removably coupled to the fixture with the used cable assembly disposed in the coupling device;

DETAILED DESCRIPTION

Referring to the Figures wherein like numerals indicate like or corresponding parts throughout the several views, systems and methods of reprocessing medical devices are shown. Many medical devices include components that are arranged in a desired orientation prior to use. During use, the components become separated. The systems and methods set forth herein receive these components in a separated condition, clean the components, rearrange the components in the desired orientation and recouple the components to return the medical device to a reusable condition.

The used medical devices are received from one or more hospitals. Once the used medical devices arrive at the facility, the used medical devices may be cleaned with a variety of processes, such as automated and/or manual cleaning processes. Depending on the condition of the used medical device, the used medical device may be also restored. The step of restoration may include sharpening edges, removing burrs, and/or rebuilding the used medical device. The restored medical device may be tested using one or more of the following testing systems: electrical profiling, examining high-speed rotation, measuring curvature, evaluating pressure decay, or other device-specific functional tests.

The used medical device may be repackaged. For example, the used medical device may be packaged after recoupling and/or after restoration. The used medical device may also be sterilized. The sterilization step may be concurrent with, or after, the step of repackaging the used medical device. One exemplary sterilization process includes exposing the used medical device to a sterilizing gas, such as ethylene oxide.

Figure 1:
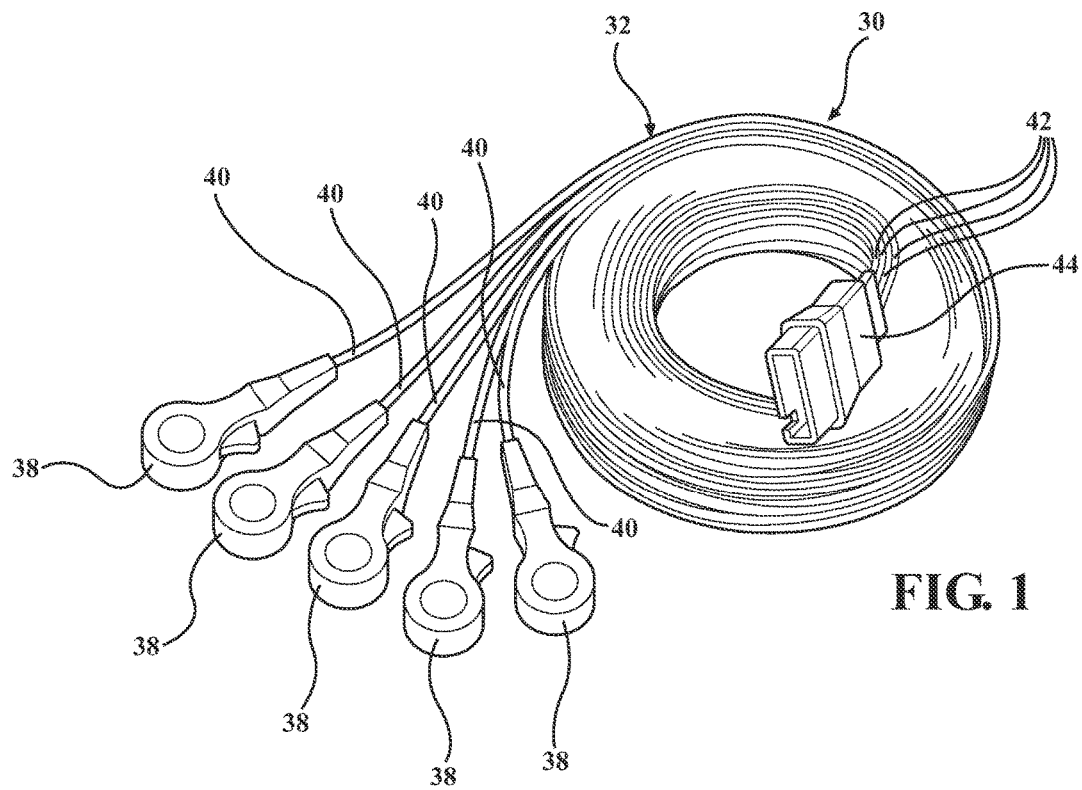
FIG. 1 is a perspective view of a unused cable assembly with a plurality of strands coupled to each other.

As shown in FIG. 1, one example of the medical device is an unused cable assembly 30 including a plurality of components coupled in a desired orientation during an original manufacturing process. The plurality of components include two or more strands 32. In one example, the unused cable assembly 30 is intended for use with an electrocardiography device. However, it is to be appreciated that the unused cable assembly 30 may be used with different types of medical devices, such as pulse oximeters and catheters. It is to be appreciated that the plurality of components may include any number of strands 32. Other exemplary medical devices are not cable assemblies and those devices can include other non-cable or non-strand components coupled to one another in a desired configuration.

Figure 2:
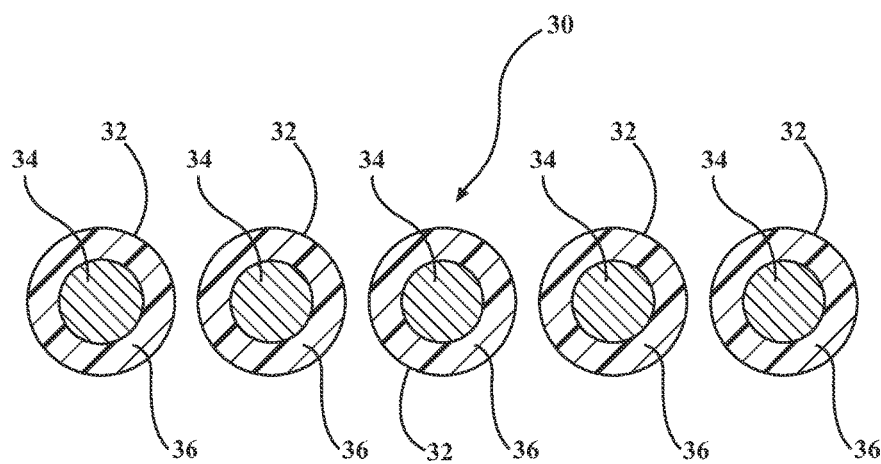
FIG. 2 is a top cross-sectional view of the plurality of strands of the unused cable assembly of FIG. 1.
Figure 3:
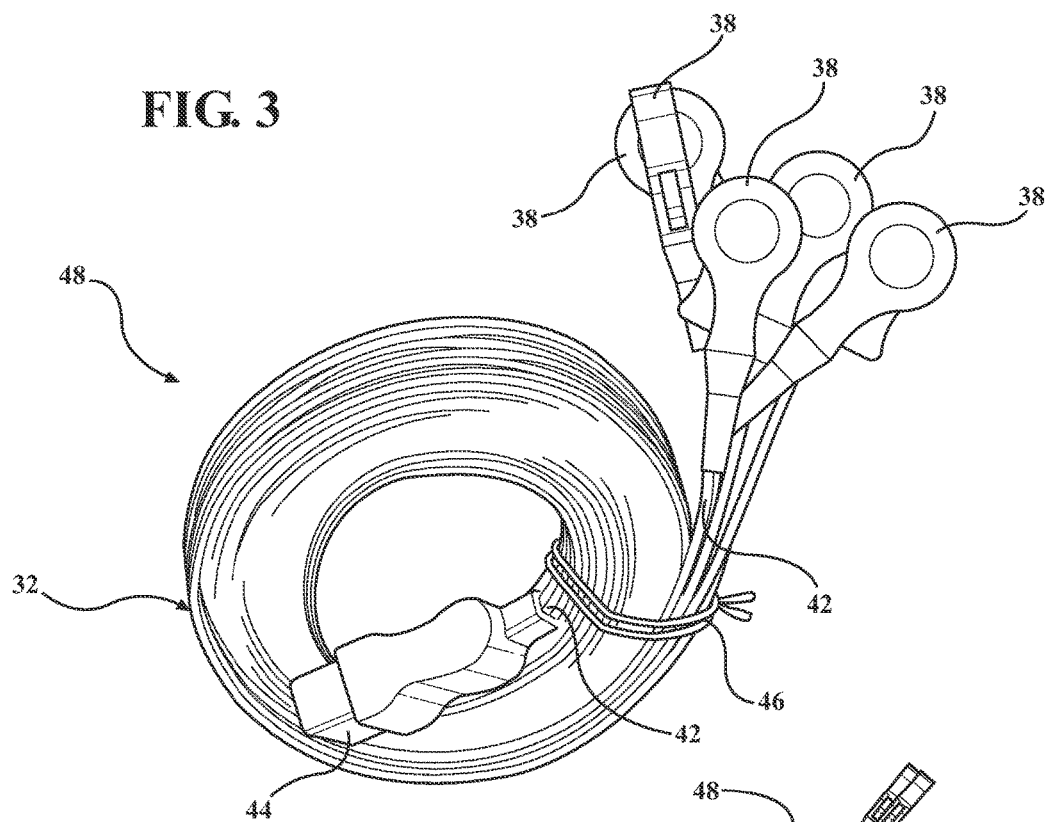
FIG. 3 is a perspective view of a used cable assembly having the plurality of strands coupled to each other by a wire tie.

As shown in FIG. 2, each one of the strands 32 includes a conductor 34 for transferring information. In one embodiment, the conductor 34 comprises a conductive material, such as copper. It is to be appreciated that the conductor 34 may be any suitable medium for transferring signals, such as a wire or a cable. The conductor 34 may take many forms. For example, the conductor 34 may be braided. Alternatively, each of the plurality of strands 32 may comprises an optical transmission device, such as a fiber-optic cable.

Each one of the strands 32 includes a coating 36 surrounding the conductor 34. The coating 36 may protect the conductor 34 from external damage. The coating 36 may be applied in many different ways, such as with extrusion or dip-coat techniques. The coating 36 may also insulate the conductor 34 and protect the conductor 34 from environmental elements that may damage or corrode the conductor 34. It is to be appreciated that the coating 36 may comprise any suitable type of material such as nylon, polyvinyl chloride, silicone, and other polymeric materials. It is to be further appreciated that the coating 36 may comprise other suitable materials, such as cloth or tape.

During the original manufacturing process that is used to form the unused cable assembly 30, the plurality of strands 32 are coupled to each other by an original binder applied to the coatings 36 of the plurality of strands 32. Alternatively, during the original manufacturing process that is used to form the unused cable assembly 30, the coatings 36 are formed together or pressed against each other before the polymer of the coatings 36 hardens to couple the plurality of strands 32 to each other.

Turning back to FIG. 1, the unused cable assembly 30 may also include a plurality of fittings 38 attached to a corresponding one of the strands 32. Each of the plurality of strands 32 has a first end 40 with the fitting 38 attached to the first end 40. Specifically, the fitting 38 is attached to the conductor 34 placing the fitting 38 in communication, such as optical or electrical communication, with the conductor 34. It is to be appreciated that the unused cable assembly 30 may include a single fitting attached to each one of the strands 32.

In one example, the fitting 38 is an electrode for use with electrocardiography devices to monitor a patient. Such an electrode is configured to be attached to the patient to monitor electrical activity. It is to be appreciated that the fitting 38 may be any other suitable Fitting 38, such as a pulse oximeter sensor, electrocardiography sensor, and catheter sensor.

The unused cable assembly 30 may also include a connector 44. The connector 44 may be attached to the plurality of strands 32. Each one of the strands 32 has a second end 42 spaced from the first end 40. The connector 44 is attached to the second ends 42 of the strands 32 such that there is a single connector for the plurality of strands 32. It is to be appreciated that the unused cable assembly 30 may include a plurality of connectors such that each of the plurality of strands 32 has a separate connector.

In one example, the connector 44 is an electrical connector. The connector 44 is in electrical communication with the conductor 34 and fitting 38 through the conductor 34. In another example, the connector 44 is in optical communication with the conductor 34 and fitting 38 through the conductor 34. Furthermore, it should be appreciated that a variety of different connector types are contemplated.

The connector 44 is coupled to a monitoring device (not shown) or console. The connector 44 places the conductors 44 in communication with the monitoring device. In one example, the conductors 34 place the fittings 38 and connector 44 in electrical or optical communications with each other such that the monitoring device is in communication with the fittings 38. In another example, the second ends 42 may not be attached to one connector, but rather each one of the second ends 42 can be attached to a corresponding one of individual connectors 50 that are in turn individually coupled to the monitoring device.

Each one of the strands 32 has a discrete length defined between the first and second ends 40, 42. The discrete lengths of the strands 32 may include the fittings 38 and the connector 44 at the first end second ends 40, 42. Exemplary, discrete lengths may range from 1 cm to 500 cm, 1 cm to 300 cm, 10 cm to 200 cm, or 50 cm to 150 cm. However, the strands 32 can have any suitable length.

The ends 40 of the strands 32 may be completely or partially separated from each other. For example, the ends 40 of the strands 32 may only be separated from each other by less than 25% of the length relative to the fittings 38 to place the fittings 38 at separate positions on a patient. Alternatively, the ends 40 of the strands 32 may be separated by less than 50%, or less than 75%, of the length relative to the fittings 38 to place the fittings 38 at separate positions on a patient.

A non-limiting exemplary method of recoupling the plurality of strands 32 of the used cable assembly 48 in the desired orientation during reprocessing is provided. The strands 32 are recoupled using a fixture 50, 150 (FIGS. 7 and 13, respectively) and a binder 52. The binder 52 is an adhesive for recoupling the strands 32 together in the desired orientation. It is to be appreciated that the binder 52 may be any type of adhesive, such as an epoxy, polyurethane, or silicone.

Figure 4:
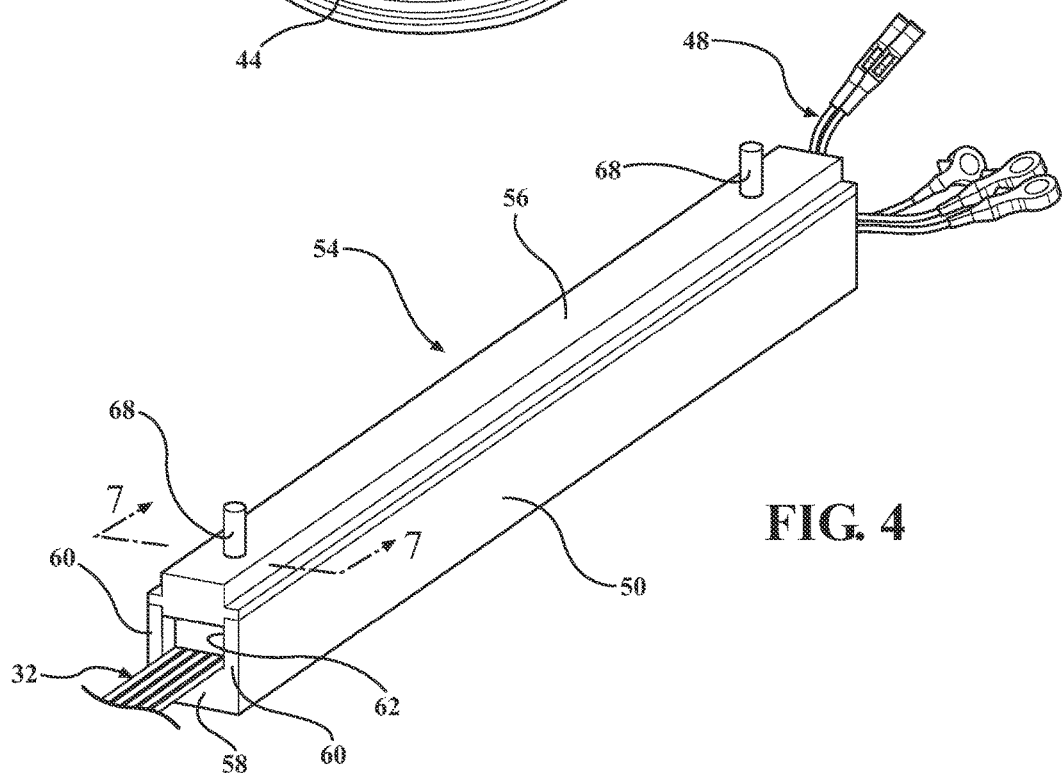
FIG. 4 is a perspective view of one non-limiting example of a coupling device including a fixture and a manifold removably coupled to the fixture with the used cable assembly disposed in the coupling device.
Figure 5:
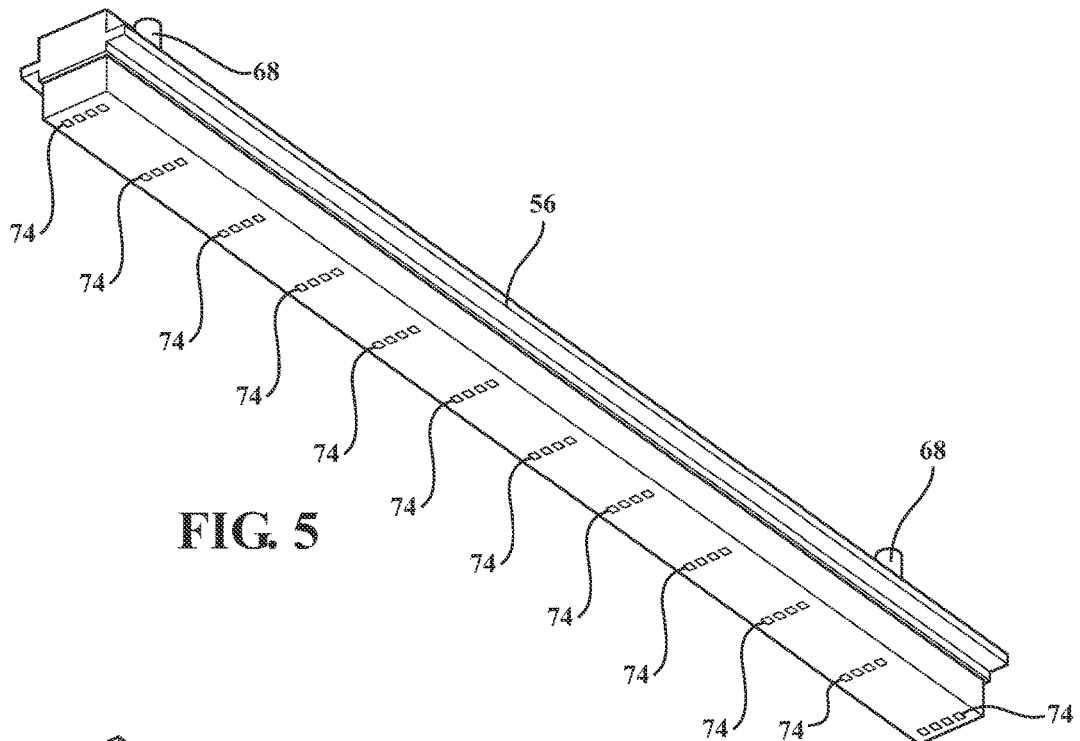
FIG. 5 is a bottom perspective view of the manifold of FIG. 4, illustrating the manifold defining a plurality of ports.
Figure 6:
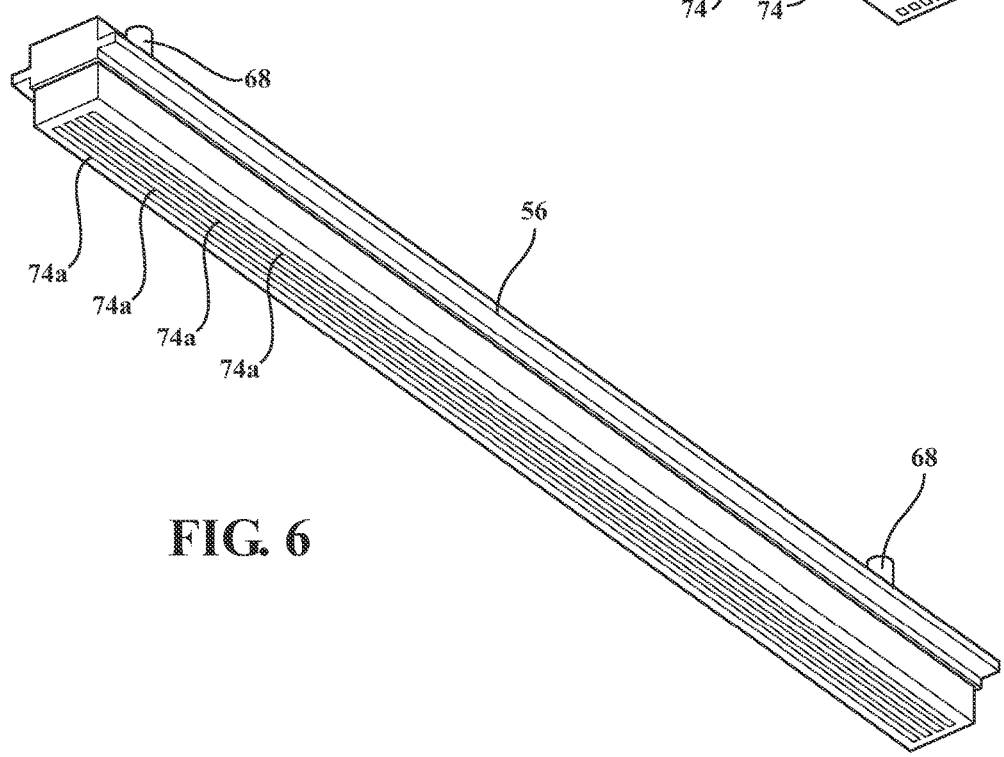
FIG. 6 is a bottom perspective view of another non-limiting example of the manifold of FIG. 4, illustrating the manifold defining a plurality of ports with an elongated configuration.
Figure 7:
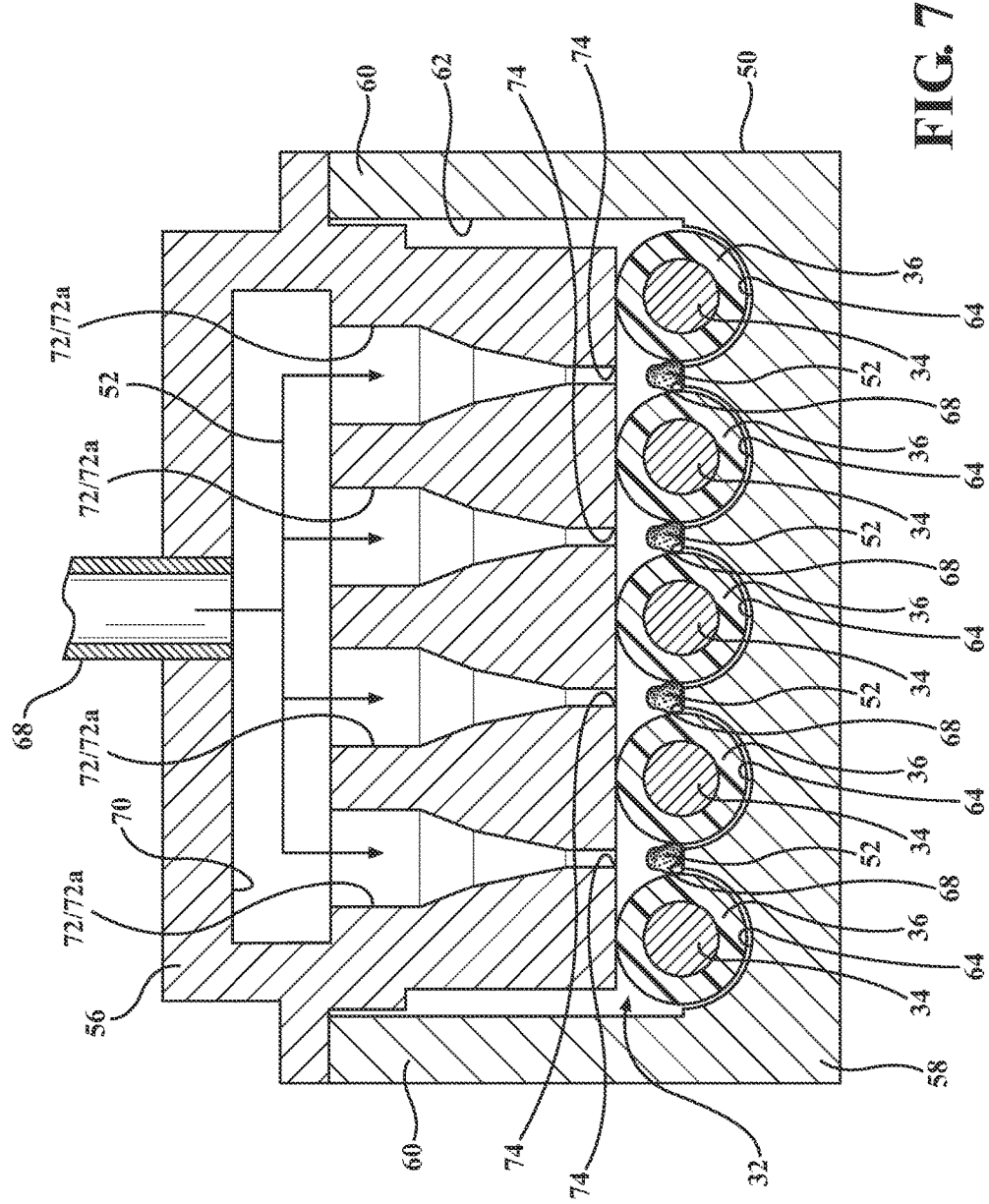
FIG. 7 is a cross-sectional view of the coupling device of FIG. 4 as taken along line 7-7 and illustrating the plurality of ports and a binder disposed on the plurality of strands.

Referring to FIGS. 4-7, a first coupling device 54 is configured to recouple the strands 32 together after complete or partial separation. The first coupling device 54 includes the fixture 50 and a manifold 56 removably coupled to the fixture 50. Referring specifically to FIGS. 4 and 7, the fixture 50 has a body 58 and a pair of flanges 60 extending upwardly from the body 58. The pair of flanges 60 are spaced from each other to define a manifold channel 62. The used cable assembly 48 is disposed in the first coupling device 54 between the fixture 50 and the manifold 56 to recouple the strands 32 to one another in the desired orientation.

As shown in FIG. 7, the fixture 50 defines a plurality of separate grooves 64. Specifically, grooves 64 are defined in the body 58 in communication with the manifold channel 62. Each one of the strands 32 is placed in a corresponding one of the grooves 64 so as to arrange the strands 32 in the desired orientation. The manifold 56 abuts the strands 32 as the manifold 56 is coupled to the fixture 50 to retain the strands 32 in the corresponding grooves 64. Alternatively, the fixture 50 may include a clamping device (not shown) to hold the strands 32 in the corresponding grooves 32. The number of grooves 64 is equal to or greater than the number of strands 32 of the used cable assembly 48.

The strands 32 are disposed in the grooves 64 parallel to each other. Specifically, the fixture 50 defines the grooves 64 in the body 58 parallel to each other. It is to be appreciated that the fixture 50 may define the grooves 64 in the body 58 in any suitable alternative configuration, such as angled relative to each other.

The fixture 50 defines the grooves 64 in the body 58 such that a gap 66 is defined between adjacent strands 32. Accordingly, the strands 32 are spaced from each other and do not abut each other when the strands 32 are disposed in the corresponding grooves 64. It is to be appreciated that the fixture 50 may define the grooves 64 in the body 58 such that adjacent strands 32 abut each other.

The fixture 50 may have a fixture length defined relative to the discrete length of the strands 32. Specifically, the fixture length of the fixture 50 is defined such that the fittings 38 and the connector 40 are disposed outside of respective ends of the fixture 50 when the strands 32 are disposed in the fixture 50 during the recoupling step. Said differently, the fixture 50 has a length such that the fittings 38 and the connector 40 are not disposed in the manifold channel 62. The fixture length may be any suitable length and may vary depending on the discrete length of the strands 32. Specifically, the fixture length of the fixture 50 will be defined by the discrete length of the plurality of strands 32 and may vary between different types of used cable assemblies 48. Non-limiting exemplary fixture lengths may range from 1 cm to 450 cm, 1 cm to 250 cm, 5 cm to 150 cm, or 40 cm to 125 cm in length. However, the fixture lengths may be any suitable length.

As best shown in FIG. 7, the manifold 56 includes a binder conduit 68 for delivering the binder 52 to the manifold 56. Additionally, the manifold 56 defines a manifold chamber 70 in communication with the binder conduit 68. Further, the manifold 56 defines a plurality of ports 72 in communication with the manifold chamber 70. The manifold 56 defines a plurality of discharge openings 74 aligned with the gaps 66 between the strands 32. Specifically, each one of the discharge openings 74 is in communication with a corresponding one of the ports 72 and is aligned with one of the gaps 66.

The ports 72 dispense the binder 52 on at least one of the strands 32. The binder 52 flows from the binder conduit 68 into the manifold chamber 70. The binder 52 then flows from the manifold chamber 70 into the plurality of ports 72. The binder 52 then is dispensed from the discharge openings 74 and is deposited on the strands 32. The binder 52 may flow under the force of gravity or may be pressurized.

Figure 13:
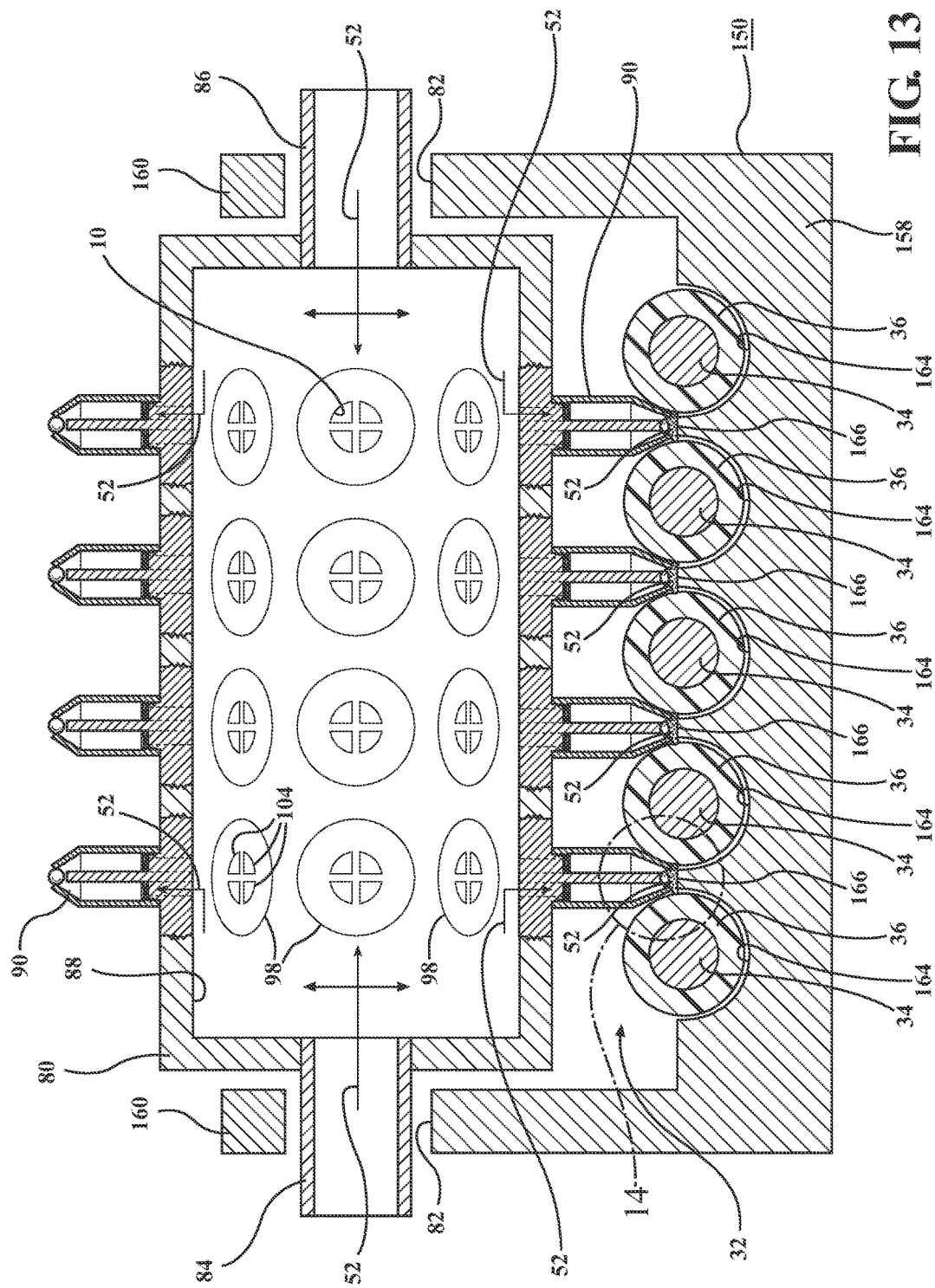
FIG. 13 is a cross-sectional view of the container of FIG. 11 as taken along line 13-13, illustrating the container having a plurality of dispensers and defining a container chamber in communication with the first and second conduits.
Figure 15:
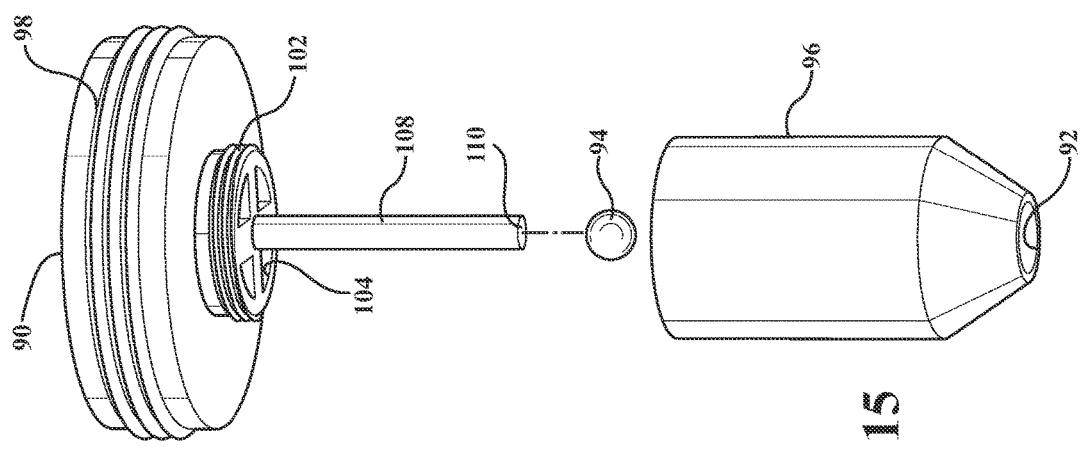
FIG. 15 is an exploded perspective view of one of the plurality of dispensers including a mounting portion and a housing defining an opening.

The ports 72 dispense the binder 52 between adjacent strands 32 to recouple the plurality of strands 32 together in the desired orientation. The binder 52 flows from the ports 72 and is deposited in the gaps 66 defined between the adjacent strands 32. The binder 52 abuts the adjacent strands 32 to recouple the strands 32 together. It is to be appreciated that the arrows designating binder 52 in FIG. 7 and FIG. 13 are provided for illustrative purposes only. The arrows designating binder 52 show the likely direction of flow of binder to its ultimate point of dispensing. However, FIGS. 7 and 13 should not be construed to imply any necessary flow path, but merely to provide an exemplary flow path that could be used in the fixture 50, 150.

Figure 8:
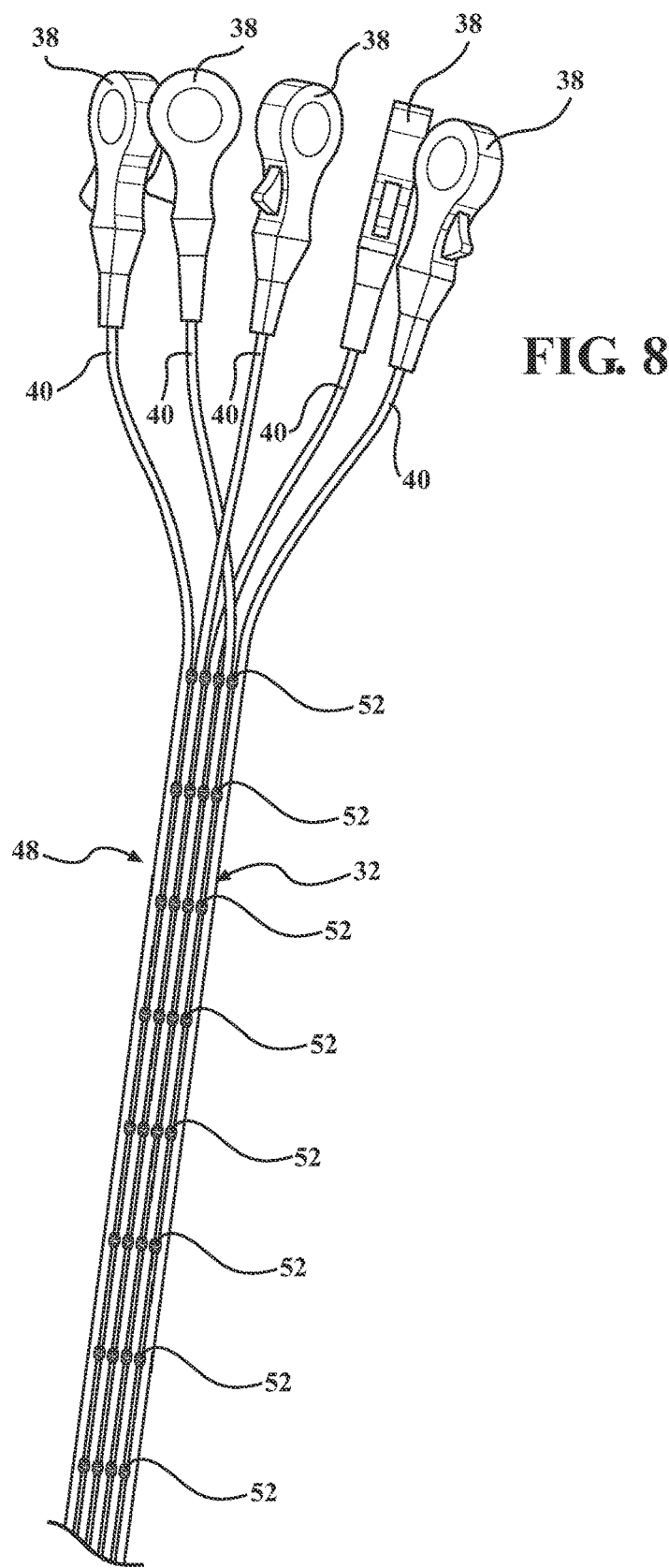
FIG. 8 is a partial perspective view of the used cable assembly of FIG. 4, illustrating the used cable assembly including the plurality of strands coupled to each other by a plurality of deposits spaced longitudinally from each other along the plurality of strands.

As shown in FIG. 8, in one example of the manifold 56, the binder 52 is applied on the strands 32 in a plurality of deposits spaced longitudinally from each other along the strands 32. The deposits of binder 52 are spaced longitudinally from each other along the strands 32 from the fittings 38 toward the connector 44. The deposits of binder 52 reduce the force required by the end user to separate the plurality of strands 32 from each other and reduce the amount of binder 52 needed relative to an application of a continuous bead of binder. Turning back to FIG. 6, in order to dispense the binder 52, the ports 72 may have a rectangular configuration at the discharge openings 74 and the ports 72 may be spaced from each other. It is to be appreciated that the ports 72 may have any suitable alternative configuration at the discharge openings 74, such as a circular or other non-rectangular configuration.

Figure 9:
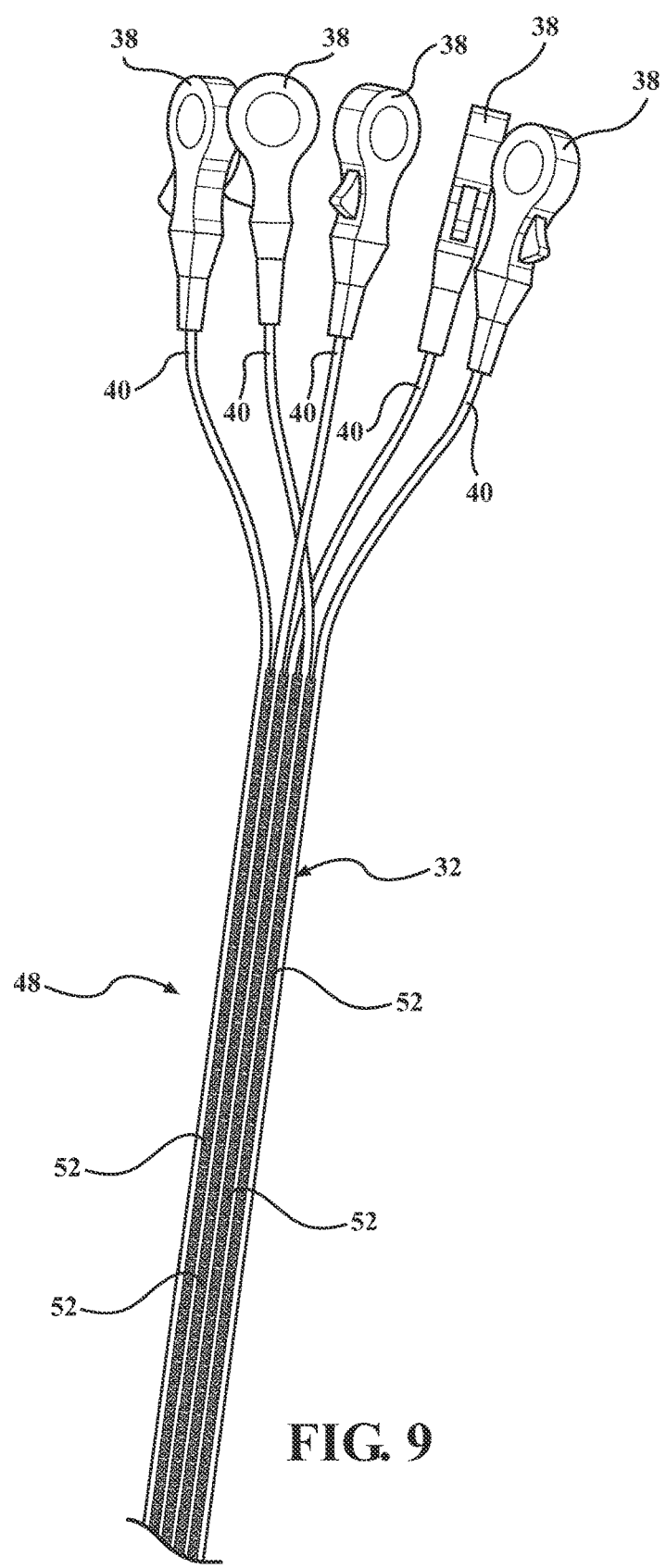
FIG. 9 is a partial perspective view of the used cable assembly of FIG. 4, illustrating the used cable assembly including the plurality of strands coupled to each other by continuous beads of binder.

As shown in FIG. 9, in another example of the manifold 56, the binder 52 is applied along the strands 32 to form a continuous bead of binder 52 on the strands 32. Specifically, the binder 52 is applied on the strands 32 between adjacent strands to form continuous beads of binder 52. The continuous beads of binder 52 extend along the strands 32 from the fittings 38 towards the connector 44. Turning back to FIG. 6, in order to dispense the continuous bead of binder 52, the ports 72a have elongated discharge openings 72a.

As shown in FIG. 10, in certain examples, a tear cavity 76 is formed in an end 78 of the binder 52 to facilitate separation of the plurality of strands 32 from each other. Specifically, the tear cavity 76 is formed in the end 78 of the continuous bead of binder 52. The manifold 56 has a tear cavity feature for forming the tear cavity 76 in the binder 52. One non-limiting example of the tear cavity feature can be the dispenser 90 (FIG. 13) or nozzle being pressed into the end 78 of the bead of binder 52 without binder being dispensed from the dispenser, so as to form an impression or recess in the end of the bead. However, the fixture 50 can have various other suitable tear cavity features. In this example, the tear cavity 76 is defined having with a v-shaped configuration. The tear cavity 76 focuses a force applied by the end user to facilitate separation of the plurality of strands 32 from each other.

Figure 12:
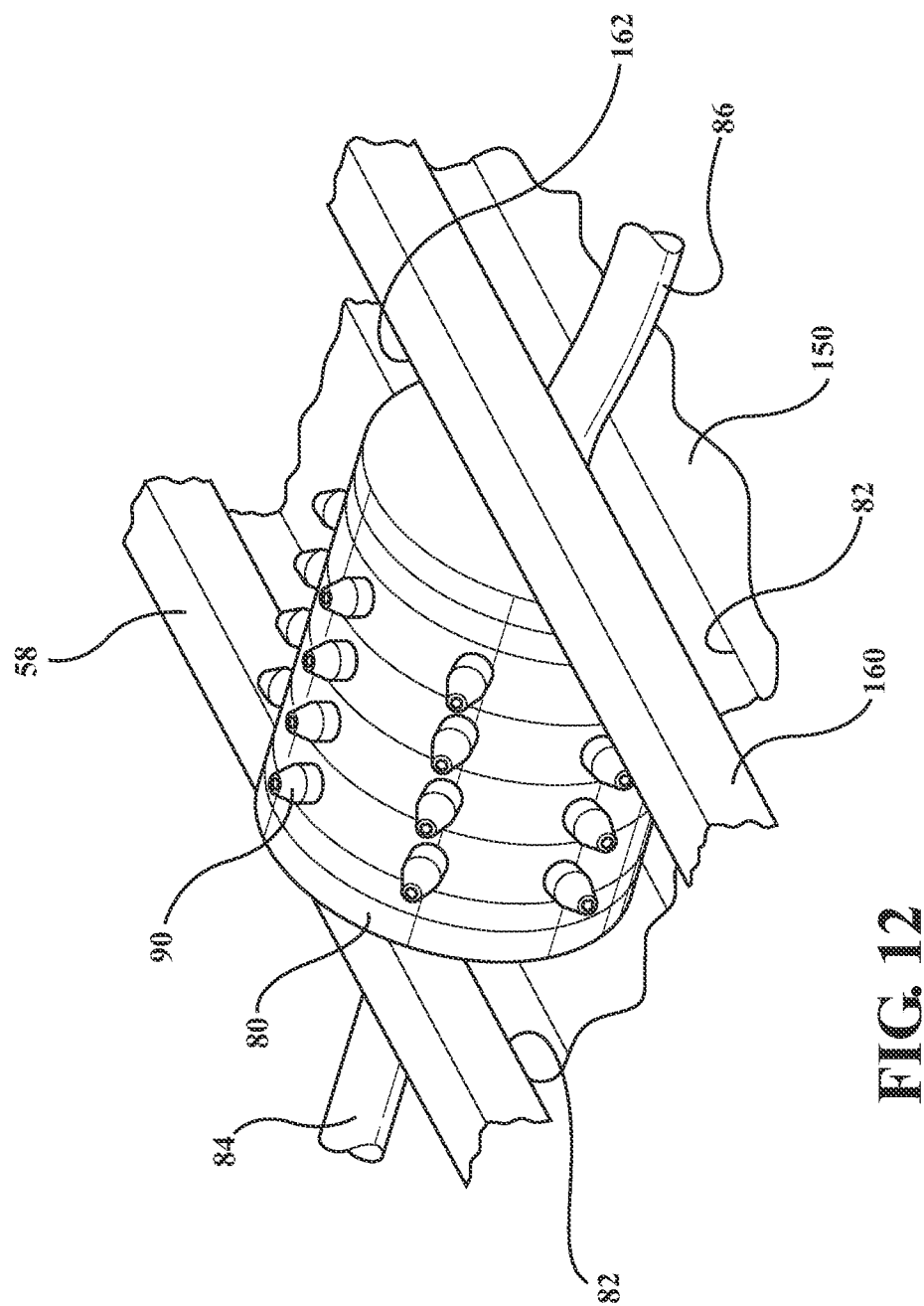
FIG. 12 is a top partial perspective view of the coupling device of FIG. 11, illustrating the coupling device including a first conduit coupled to the container and a second conduit coupled to the container opposite of the first conduit.

As shown in FIGS. 11 and 12, another non-limiting example of a coupling device 159 for recoupling the strands 32 of the used cable assembly 48 in a desired orientation is provided. The second coupling device 154 includes a fixture 150 and a container 80 movably coupled to the fixture 150. The fixture 150 has a body 158 and a pair of flanges 160 extending upwardly from the body 158 with the pair of flanges 160 spaced from each other. The fixture 150 defines a container channel 162 between the pair of flanges 160. Additionally, the fixture 150 defines a conduit channel 82 in one of the flanges 160.

As shown in FIG. 13, like fixture 50, the fixture 150 defines a plurality of separate grooves 164. Specifically, the separate grooves 164 are defined in the body 158 in communication with the container channel 162. The strands 32 are placed in the grooves 164 to arrange the strands 32 in a corresponding one of the grooves 164. Thus, the number of grooves 164 is equal to or greater than the number of strands 32 of the used cable assembly 48. However, the fixture 150 can have any number of grooves.

The fixture 150 defines the grooves 164 in the body 158 parallel to each other so as to place the strands 32 parallel to each other. It is to be appreciated that the fixture 50 may define the grooves 64 in the body 58 in any suitable alternative configuration, such as angled relative to each other.

The fixture 150 defines the grooves 164 in the body 158 such that a gap 166 is defined between adjacent strands 32. Accordingly, the strands 32 are spaced from each other and do not abut each other when the strands 32 are disposed in the grooves 164. It is to be appreciated that the fixture 150 may define the grooves 164 in the body 158 such that adjacent strands 32 of the strands 32 abut each other.

As best shown in FIG. 13, the container 80 includes a first conduit 84 and a second conduit 86 for delivering the binder 52 to the container 80. As described above the binder 52 may be pressurized by a pressure source to force the binder 52 into the container 80 and onto the plurality of strands 32. The pressure source may be pressurized air or any other suitable alternative, such as nitrogen or mechanical pressure.

The container 80 holds a volume of binder 52 to the fixture 150. Specifically, the container 80 defines a container chamber 88 with volume of binder 52 disposed in the container chamber 88. The container chamber 88 is in communication with the first and second conduits 84, 86.

Figure 14:
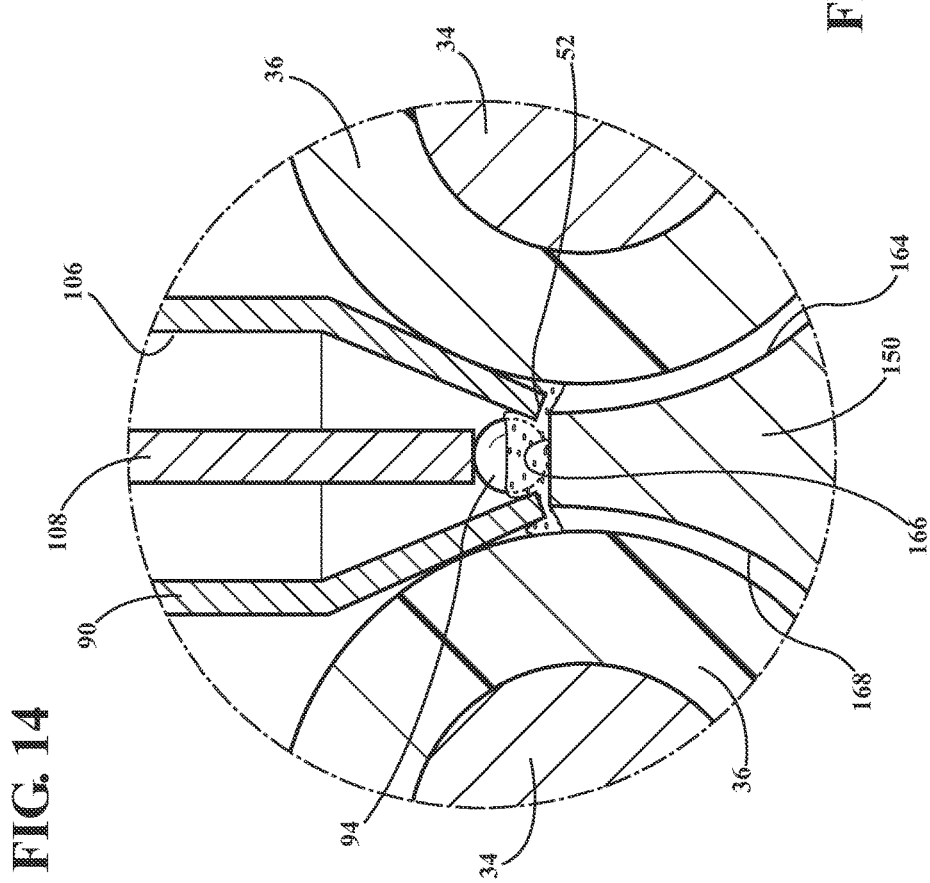
FIG. 14 is a partial cross-sectional view of one the plurality of dispensers in FIG. 13, illustrating one the plurality of dispensers contacting the fixture.

The container 80 includes a plurality of dispensers 90 extending in communication with the container channel 162. Each one of the dispensers 90 defines a discharge opening 92 aligned with a corresponding one of the gaps 166 defined between the strands 32. The dispensers 90 extend into the container channel 162. The dispensers 90 are in communication with the container chamber 88. As shown in FIG. 14, each of the plurality of dispensers 90 is disposed in one of the gaps 166 defined between the adjacent strands 32.

As shown in FIGS. 15-19, each one of the dispensers 90 includes a ball 94 and a housing 96 defining the discharge opening 92 with the ball 94 movably disposed in the discharge opening 92 to dispense the binder 52 on at least one of the strands 32. Each one of the dispensers 90 includes a mounting portion 98 coupled to housing 96. The housing 96 extends from the mounting portion 98 into the container channel 162. The housing 96 and mounting portion 98 are comprised of metal. It is to be appreciated that the housing 96 and mounting portion 98 may comprise any suitable material, such as plastic.

Figure 16:
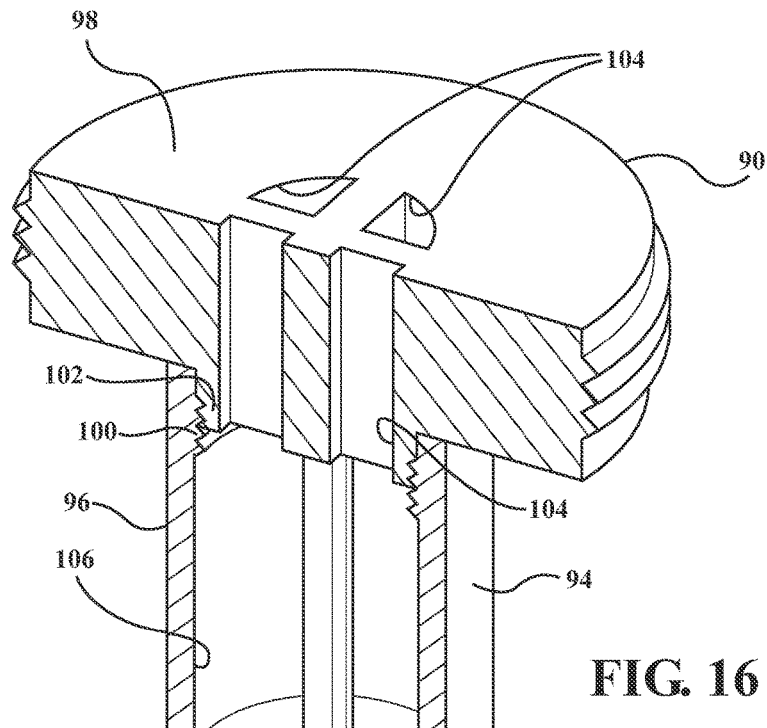
FIG. 16 is a perspective cross-sectional view of one of the plurality of dispensers of FIG. 13, illustrating the dispenser including a rod extending from the mounting portion and a ball disposed in the housing abutting the rod.

As shown in FIG. 16, the housing 96 has a first set of threads 100 and the mounting portion 98 has a second set of threads 102 with the first set of threads 100 engaging the second set of threads 102 to mount the housing 96 to the mounting portion 98. It is to be appreciated that the housing 96 may be mounted to the mounting portion 98 in any suitable method, such as by press fitting the housing 96 on the mounting portion 98. In other examples, the housing can be an integral portion of the mounting portion.

Figure 17:
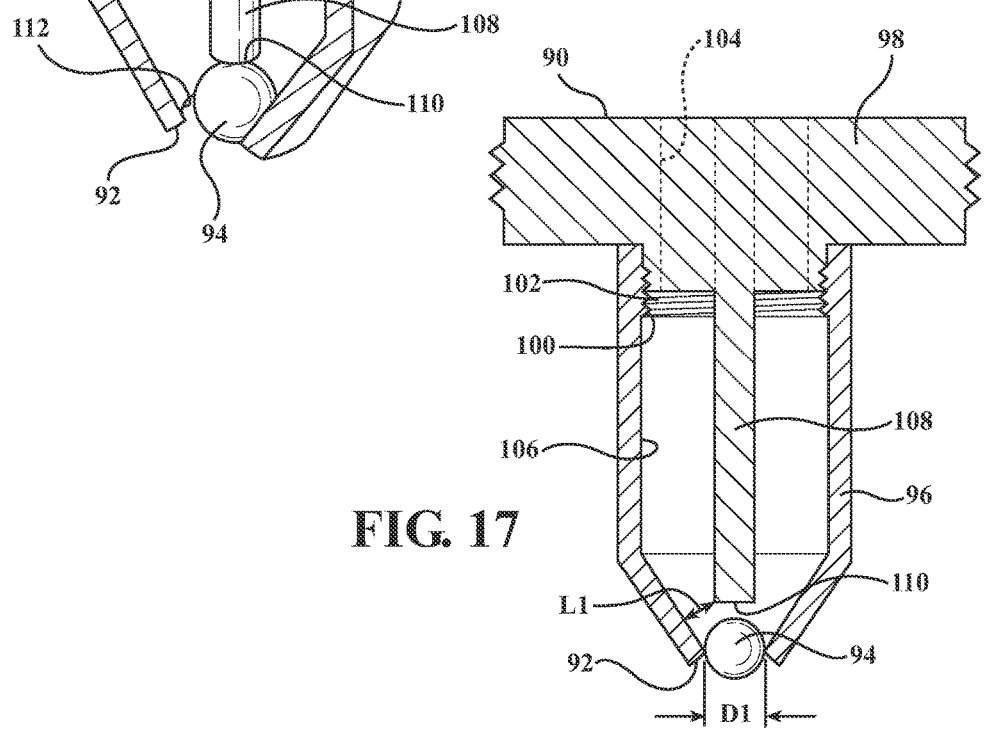
FIG. 17 is a plan cross-sectional view of one of the plurality of dispensers of FIG. 13, illustrating the ball spaced from the rod and disposed in the opening.
Figure 18:
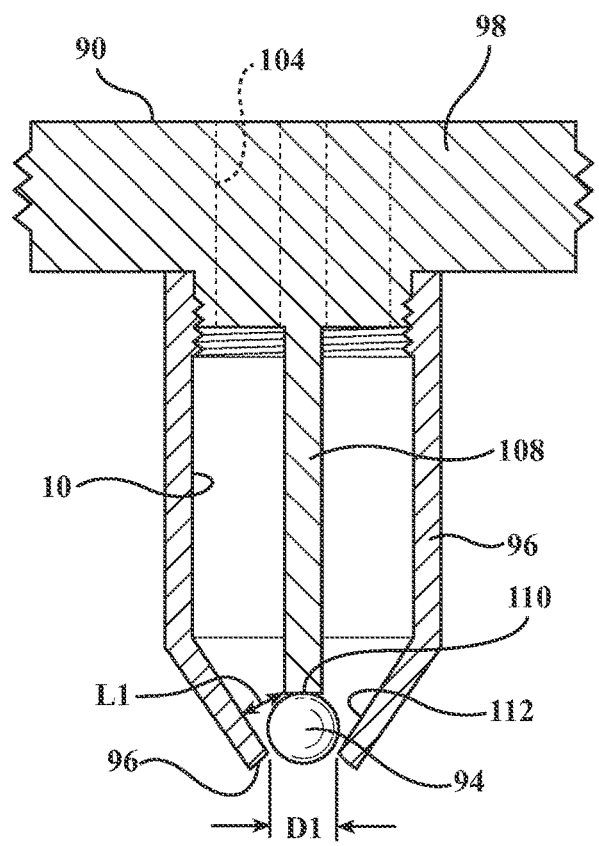
FIG. 18 is a cross-sectional view of one of the plurality of dispensers of FIG. 13, illustrating the ball spaced from the opening to define a void between the ball and the housing.
Figure 19:
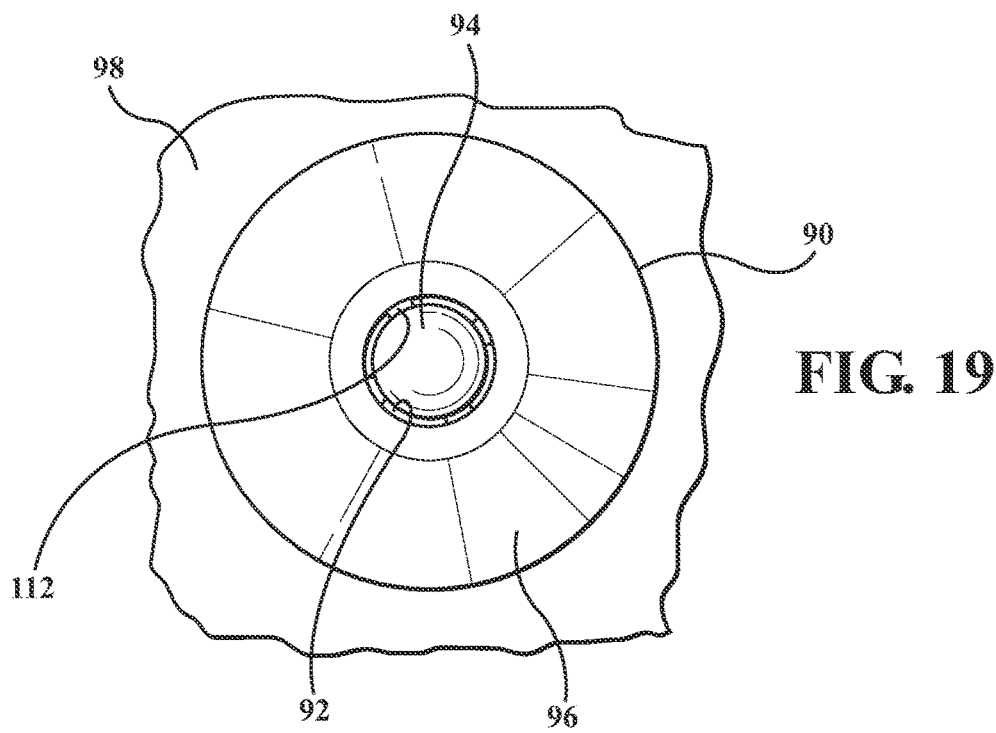
FIG. 19 is a plan view of one of the plurality of dispensers of FIG. 13, illustrating the ball spaced from the opening to define the void between the ball and the housing.

As shown in FIGS. 13 and 16, the mounting portion 98 defines apertures 104 in communication with the container chamber 88. Turning to FIGS. 17 and 18, the housing 96 defines a dispenser chamber 106 in communication with the apertures 104.

Referring to FIGS. 14-18, each one of the dispensers 90 includes a stopper rod 108, which is fixed to the mounting portion 98 and extends into the dispenser chamber 106. The stopper rod 108 has a rod end 110 with a distance L1 defined between the rod end 110 of the stopper rod and the housing 96.

The ball 94 is movably disposed in the dispenser chamber 106 and movably disposed in the discharge opening 92. The ball 94 has a diameter D1 which is greater than distance L1 and the diameter of the discharge opening 92. As shown in FIG. 18, the housing 96 and ball 94 define a void 112 therebetween when the ball 94 is spaced from the discharge opening 92.

The binder 52 flows from the first and second conduits 84, 86 into the container chamber 88. The binder 52 in the container chamber 88 is pressurized by the pressure source and applies pressure to the ball 94 such that the ball 94 is seated in the discharge opening 92.

The dispensers 90 dispense the binder 52 on at least one of the strands 32 as the container 80 moves along the fixture 150. More specifically, the container 80 may rotate or roll along the fixture 150. As the container 80 rolls along the fixture 150, different rows of the dispensers 90 sequentially contact the fixture 150 and the balls 92 of the particular row of the dispensers 90 adjacent to the strands 32 are moved from the discharge openings 92 into the dispenser chambers 102 and abut the rod ends 110. The diameter D1 of the balls 92 are greater than the distances L1 between the rod ends 110 and the housing 96 such that the balls 94 are retained in the dispenser chambers 102 relative to the rod ends 110 and discharge openings 92.

As best shown in FIG. 14, the voids 112 are defined between the balls 92 and housings 96. As the balls 92 contact the fixture 150 and move into the dispenser chambers 102, the binder 52 in the dispenser chambers 102 flows through the voids 112 and discharge openings 92 to be deposited on the plurality of strands 32.

Moving the container 80 along the fixture 150 dispenses the binder 52 in a plurality of deposits spaced from each other along the strands 32 as shown in FIG. 10. The deposits of binder 52 are spaced longitudinally from each other along the strands 32 from the fittings 38 towards the connectors 44.

As described above with respect to fixture 50 of FIG. 4, the fixture 150 of FIG. 11 has a fixture length defined relative to the discrete length of plurality of strands 32. Specifically, the fixture length of the fixture 150 is defined such that the fittings 38 and connector 40 are disposed outside of the fixture 150 when the strands 32 are disposed in the fixture 150. Said differently, the fittings 38 and connector 40 are not disposed in the container channel 162 during the step of recoupling. The fixture length may be any suitable length and may vary depending on the discrete length of the strands 32. Furthermore, the fixture length may vary between different types of used cable assemblies 48 as described above with respect to fixture 50.

Figure 20:
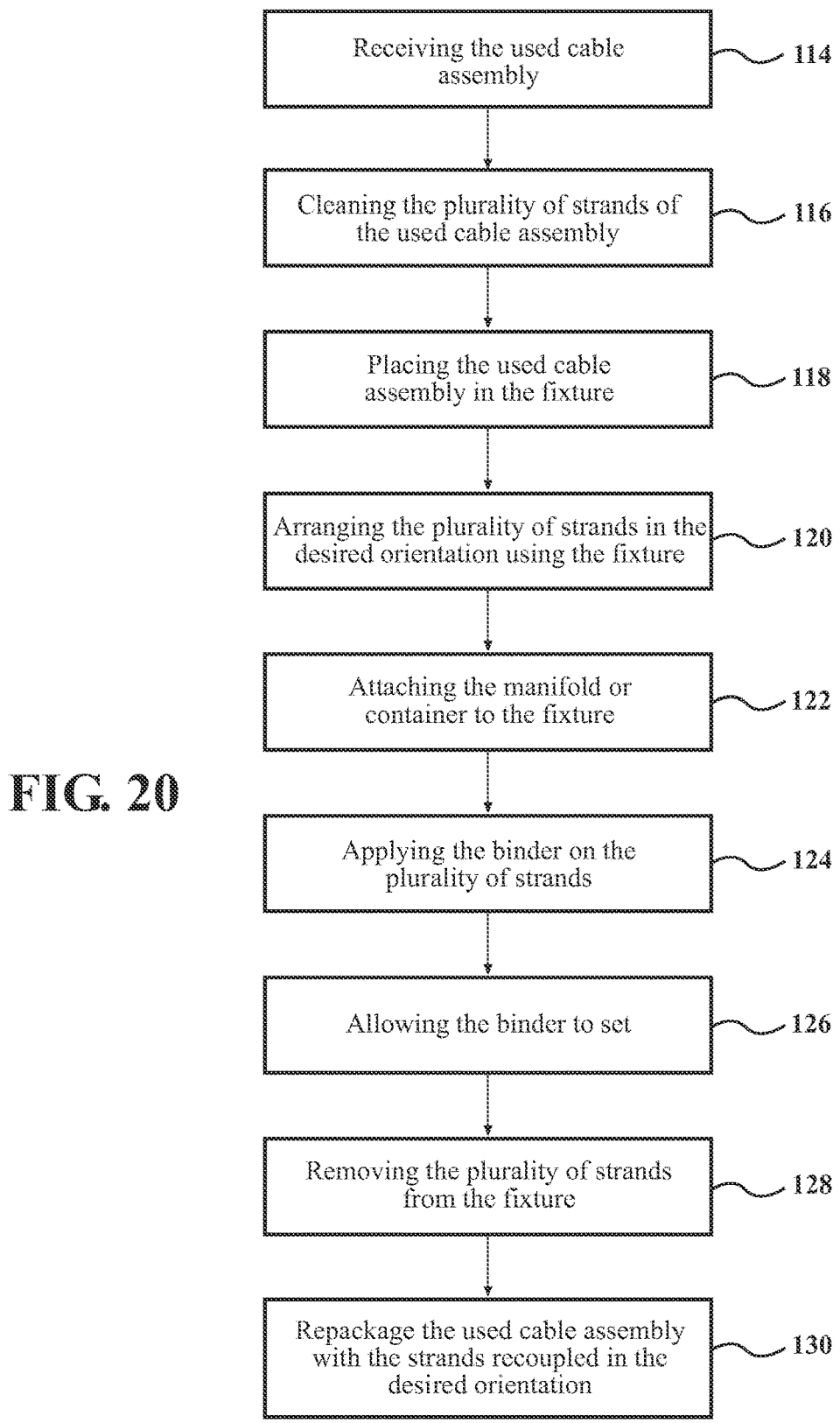
FIG. 20 is a flow chart of one non-limiting example of a method of recoupling the plurality of strands of the used cable assembly of FIG. 3 to each other in a desired orientation.

Referring to FIG. 20, a flow chart of an exemplary method for recoupling the components of the medical device in the desired orientation during reprocessing of the medical device is provided. In step 114, the medical device is received with the components of the medical device in the separated condition with the components spaced from the desired orientation. More specifically, with respect to the second example of the medical device, the used cable assembly 48 is received with the plurality of strands 32 partially or completely separated from the each other.

In step 116, the components of the medical device are cleaned. The cleaning may include removing the coating 36 or a residual binder (not shown) from at least one of the strands 32 remaining on the used cable assembly 48. Alternatively, the cleaning may include removing dirt, oil, or other debris. The cleaning step may be carried out in an automated process or by an operator. The cleaning step may use a mechanical device, such as a scrub brush, or a chemical, such as a solvent, to remove the coating 36 or residual binder.

In step 118, the used cable assembly 48 is placed in the fixture 50, 150. Placing the used cable assembly 48 in the fixture 50, 150 may include using the clamping device to couple the used cable assembly 48 to the fixture 50, 150. Placing the used cable assembly 48 in the fixture 50, 150 may be performed by an automated process or by an operator. The fittings 38 and connector 44 are disposed outside of the fixture 50 as the used cable assembly 48 is placed in the fixture 50, 150. The connector 44 is attached to the second ends 42 of the strands 32, with the fittings 38 being electrodes in electrical communication with the connector 44. In this example, the connector 44 is configured to connect to an electrocardiography device to place the fittings in electrical communication with the same.

In step 120, the components of the medical devices are arranged in the desired orientation. Continuing with the previous example, the strands 32 are arranged in the desired orientation using the fixture 50, 150. Specifically, each one of the strands 32 is placed in a corresponding one of the grooves 64, 164. In one example, the medical device includes three or more strands 32 placed in a corresponding one of three grooves. However, the device can have more or fewer strands. The clamping device is engaged with the strands 32 to hold the strands 32 in the grooves 32. Arranging the strands 32 in the desired orientation using the fixture 50, 150 may be performed by an automated process or by an operator.

The strands 32 are disposed in the grooves 64, 164 parallel to each other. The strands 32 are spaced from each other and do not abut each other when the strands 32 are disposed in the separate grooves 64, 164 thus defining the gaps 66, 166 between adjacent pair of strands 32.

In step 122, the manifold 56 is attached to the fixture 50 or container 80 is attached to the fixture 150. Attaching the manifold 56 or container 80 to the fixture 50, 150 may be performed by an automated process or by an operator.

As one example, the manifold 56 of FIG. 7 is disposed in the manifold channel 62 and attached to the fixture 50. The plurality of ports 72 are aligned with the gaps 66 defined between adjacent strands 32.

As a further example, the container 80 of FIG. 13 is disposed in the container channel 162 and attached to the fixture 150. The dispensers 90 are aligned with the gaps 166 defined between the adjacent strands 32, with the first conduit 84 being disposed in the conduit channel 82 of one of the pair of flanges 160 and the second conduit 86 being disposed in the conduit channel 82 of the other of the pair of flanges 160.

In step 124, the binder 52 is applied to the components in the desired orientation to recouple the components and return the components to the adhered condition. In particular, the binder 52 is applied on the plurality of strands 32. Specifically, the binder 52 is an adhesive dispensed between adjacent strands 32 to recouple the strands 32 in the desired orientation. The binder 52 may be deposited in the gap 66, 166 between adjacent strands 32 or on the plurality of strands 32.

Continuing with the exemplary coupling device 54 of FIG. 7, binder 52 flows through the binder conduit 68 to the manifold 56 and is disposed in the manifold chamber 70. The binder 52 then flows from the manifold chamber 70 into the plurality of ports 72 and through the discharge openings 74 to be applied on the plurality of strands 32. The binder 52 may form a continuous bead of binder 52 and a tear cavity may be formed in an end of the continuous bead of the binder to facilitate separation of the strands from each other.

Further to the exemplary coupling device 154 of FIG. 13, binder 52 flows through the first and second conduits 84, 86 to the container 80 and is disposed in the container chamber 88. The binder 52 in the container chamber 88 then flows through the apertures 104 into the dispenser chambers 106 of the housings 96 and applies pressure to the balls 94 to seat the balls 94 in the discharge openings 92.

The container 80 rolls along the fixture 150 with the dispensers 90 temporarily contacting the fixture 150. Specifically, the balls 94 temporarily contact the fixture 150 and move from the discharge openings 92 to abut the rod ends 110 of the stopper rods 108 under the force of contact against the pressure of the binder 52. The voids 112 are defined between the balls 94 and housings 96 with the binder 52 flowing through the voids 112 and the discharge openings 92 and onto the strands 32. The binder 52 forms a plurality of deposits spaced longitudinally from each other along the strands 32.

In step 126, the binder 52 sets until the strands 32 are adhered to each other such that the strands 32 remain in the desired orientation and the used cable assembly 48 remains in the adhered condition. Setting of the binder 52 may include drying or curing the adhesive. For example, setting of the binder 52 may include applying heat, UV light, or humidity to the binder 52.

In step 128, the strands 32 are removed from the fixture 50. Removing the strands 32 from the fixture 50, 150 includes removing the manifold 56 or container 80. Removing the strands 32 from the fixture 50, 150 may be performed by an automated process or by an operator.

In step 130, the used cable assembly 48 is repackaged with the strands 32 recoupled in the desired orientation. The used cable assembly 48 is sterilized such that the used cable assembly 38 is usable in a medical environment. It is to be appreciated that the used cable assembly 48 may be sterilized prior to being repackaged, or may be sterilized after or during repackaging.

Although not specifically shown in the Figures, an additional example of the medical device is an intravenous device (not shown) including a bag (not shown) and a tube (not shown) coupled to the bag in a desired orientation during an original manufacturing process. An end user, such as a doctor or nurse, separates the tube from the bag to attach the bag to a patient during a medical procedure. After use of the tube and bag, a used tube and bag is delivered to a medical device reprocessing facility with the tube separated from the bag.

A method of recoupling the tube to the bag in the desired orientation during reprocessing is disclosed. The intravenous device is received with the tube separated from the bag. Any residual binder (not shown) or material (not shown) remaining on the tube or bag is cleaned or removed. The tube is arranged in the desired orientation on the bag. The binder is applied to the tube and bag as the tube is in the desired orientation on the bag to the tube. The binder sets until the tube is adhered to the bag such that the tube remains in the desired orientation.

It should be appreciated that the described method may be used to recouple any type of medical device where the components of the medical device become separated from one another during used. For example, the method may be used to recouple a medical device with a peeled apart sheathing such as an introducer. Another example is a single-use small, medical device that is attached beside the patient on the patient bed which may employ the use of a peelable ribbon or band that allow the device to be secured to any location. Either of these medical devices may be recoupled in accordance with the methods described above.

Several embodiments of the present invention have been described in an illustrative manner, and it is to be understood that the terminology which has been used in intended to be in the nature of words of description rather than of limitation. It is also to be understood that the steps of the disclosed method can be performed in any order. Obviously, many modifications and variations of the present invention are possible in light of the above teachings. The inventions may be practiced otherwise than as specifically described within the scope of the appended claims.

What is claimed is:

1. A method of recoupling a plurality of strands of a used cable assembly in a desired orientation using a fixture and a binder, the used cable assembly including a fitting attached to a first end of each of the plurality of strands, said method comprising the steps of:
    cleaning the plurality of strands of the used cable assembly;
    arranging the plurality of strands in the desired orientation using the fixture;
    applying the binder on at least one of the plurality of strands to recouple the plurality of strands in the desired orientation; and
    removing the plurality of strands from the fixture.

2. The method as set forth in claim 1 wherein cleaning the plurality of strands of the used cable assembly includes removing a residual binder from the at least one of the plurality of strands remaining on the used cable assembly.

3. The method as set forth in claim 1 wherein cleaning the plurality of strands of the used cable assembly includes removing a coating from the at least one of the plurality of strands.

4. The method as set forth in claim 1 wherein arranging the plurality of strands in the desired orientation is further defined as disposing each one of the plurality of strands in a corresponding one of a plurality of separate grooves defined by the fixture.

5. The method as set forth in claim 1 wherein arranging the plurality of strands in the desired orientation includes arranging each one of the plurality of strands so as to define a gap between adjacent strands.

6. The method as set forth in claim 1 wherein arranging the plurality of strands in the desired orientation includes arranging each one of the plurality of strands such that the plurality of strands are parallel to each other.

7. The method as set forth in claim 1 wherein applying the binder on the at least one of the plurality of strands is further defined as dispensing the binder between adjacent strands to recouple the plurality of strands in the desired orientation.

8. The method as set forth in claim 1 wherein applying the binder on the at least one of the plurality of strands is further defined as applying the binder on the at least one of the plurality of strands in a plurality of deposits spaced longitudinally from each other along the plurality of strands.

9. The method as set forth in claim 1 wherein applying the binder on the at least one of the plurality of strands is further defined as applying the binder on the at least one of the plurality of strands along the plurality of strands to form a continuous bead of binder.

10. The method as set forth in claim 9 including forming a tear cavity in an end of the continuous bead of binder to facilitate separation of the plurality of strands from each other.

11. The method as set forth in claim 1 including attaching a manifold having a plurality of ports to the fixture wherein the plurality of ports dispense the binder on the at least one of the plurality of strands.

12. The method as set forth in claim 1 including movably coupling a container holding a volume of binder to the fixture and moving the container along the fixture to dispense the binder on the at least one of the plurality of strands.

13. The method as set forth in claim 12 wherein moving the container along the fixture to dispense the binder on the at least one of the plurality of strands includes moving a plurality of dispensers along the fixture to dispense the binder on the at least one of the plurality of strands.

14. The method as set forth in claim 13 wherein each of the plurality of dispensers include a ball and a housing defining an opening with the ball movably disposed in the opening to dispense the binder on the at least one of the plurality of strands and moving the plurality of dispensers along the fixture to dispense the binder on the at least one of the plurality of strands includes depressing the ball in the housing to dispense the binder on the at least one of the plurality of strands.

15. The method as set forth in claim 14 wherein moving the container along the fixture to dispense the binder on the at least one of the plurality of strands includes moving the container along the fixture to dispense the binder in a plurality of deposits spaced from each other along the plurality of strands.

16. The method as set forth in claim 1 wherein the plurality of strands includes three or more strands.

17. The method as set forth in claim 1 further including sterilizing the used cable assembly after the plurality of strands are recoupled in the desired orientation.

18. The method as set forth in claim 1 further including repackaging the used cable assembly after the plurality of strands are recoupled in the desired orientation.

19. The method as set forth in claim 1 wherein the fitting is an electrode.

20. The method as set forth in claim 1 wherein the binder is an adhesive for recoupling the plurality of strands in the desired orientation.

21. The method as set forth in claim 1 wherein the used cable assembly includes a connector attached to a second end of each of the plurality of strands with the fittings in electrical communication with the connector.

22. The method as set forth in claim 21 wherein the connector is configured to connect an electrocardiography device to place the fittings in electrical communication with the electrocardiography device.

* * * * *